(12) United States Patent
Goldberg et al.

(10) Patent No.: US 8,152,801 B2
(45) Date of Patent: Apr. 10, 2012

(54) TISSUE ABLATION USING PULSE MODULATED RADIO FREQUENCY ENERGY

(75) Inventors: S. Nahum Goldberg, Brookline, MA (US); Kimbolt Young, Newtonville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1137 days.

(21) Appl. No.: 11/948,299

(22) Filed: Nov. 30, 2007

(65) Prior Publication Data

US 2008/0188849 A1 Aug. 7, 2008

Related U.S. Application Data

(60) Provisional application No. 60/868,756, filed on Dec. 6, 2006.

(51) Int. Cl.
*A61B 18/12* (2006.01)
(52) U.S. Cl. ............................................. 606/34; 606/41
(58) Field of Classification Search ................ 606/34, 606/41, 42, 48–50
See application file for complete search history.

(56) References Cited

U.S. PATENT DOCUMENTS

| 6,033,399 | A | 3/2000 | Gines |
| 6,080,149 | A | 6/2000 | Huang et al. |
| 6,183,468 | B1 * | 2/2001 | Swanson et al. ............... 606/40 |
| 6,228,081 | B1 | 5/2001 | Goble |
| 6,238,387 | B1 * | 5/2001 | Miller, III ...................... 606/34 |
| 6,379,353 | B1 | 4/2002 | Nichols |
| 6,893,435 | B2 | 5/2005 | Goble |
| 7,722,601 | B2 * | 5/2010 | Wham et al. .................... 606/34 |
| 2001/0014802 | A1 * | 8/2001 | Tu .................................. 606/21 |
| 2002/0165531 | A1 | 11/2002 | Goble |
| 2006/0293649 | A1 * | 12/2006 | Lorang et al. .................. 606/32 |

OTHER PUBLICATIONS

PCT International Search Report for PCT/US2007/086110, Applicant: Boston Scientific Scimed, Inc., Form PCT/ISA/210 and 220, dated Apr. 25, 2008 (5 pages).
PCT Written Opinion of the International Search Authority for PCT/US2007/086110, Applicant: Boston Scientific Scimed, Inc., Form PCT/ISA/237, dated Apr. 25, 2008 (6 pages).
PCT International Preliminary Report on Patentability (Chapter I of the Patent Cooperation Treaty) for PCT/US2007/086110, Applicant: Boston Scientific Limited, Form PCT/IB/326 and 373, dated Jun. 18, 2009 (8 pages).
Office Communication dated Aug. 23, 2010 for application No. 07 865 013.2, Applicant: Boston Scientific Limited, EPO Form 2906 01.91 TRI (3 pages).

* cited by examiner

*Primary Examiner* — Linda Dvorak
*Assistant Examiner* — Daniel Fowler
(74) *Attorney, Agent, or Firm* — Vista IP Law Group LLP

(57) ABSTRACT

Tissue ablation systems and methods are provided. Ablation energy (e.g., radio frequency energy) is delivered to the tissue and a physiological parameter (e.g., impedance and/or temperature) indicative of a change in moisture concentration of the tissue is sensed. The ablation energy is alternately pulsed on and off to generate an energy pulse train, with the ablation energy being pulsed on if the sensed physiological parameter crosses a threshold value indicative of an increase in the moisture concentration, and being pulsed off if the sensed physiological parameter crosses a threshold value indicative of a decrease in the moisture concentration.

40 Claims, 5 Drawing Sheets

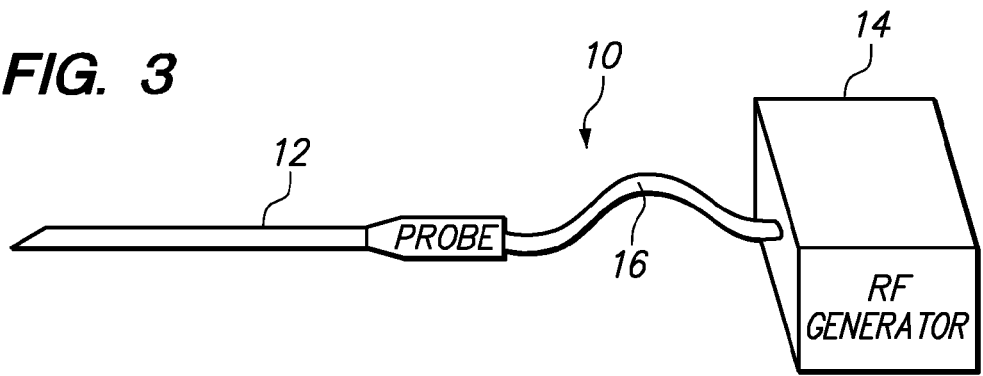
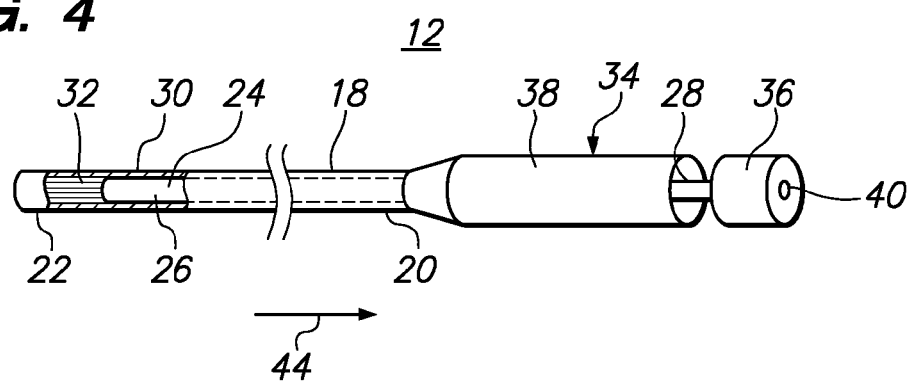
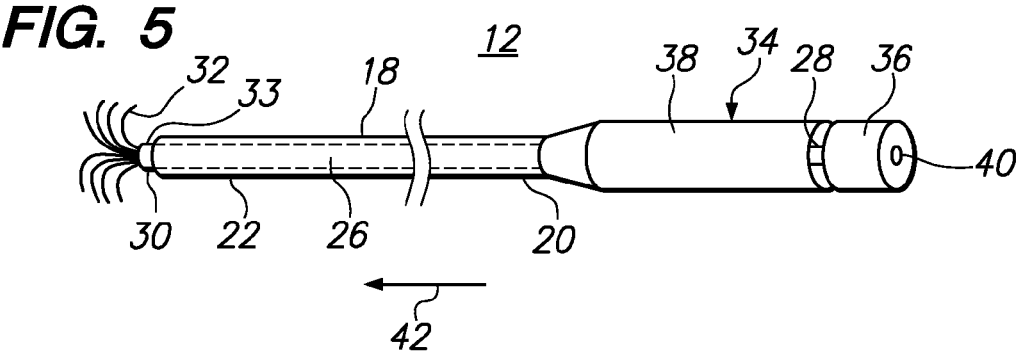

TISSUE ABLATION USING PULSE MODULATED RADIO FREQUENCY ENERGY

RELATED APPLICATION DATA

The present application claims the benefit under 35 U.S.C. §119 to U.S. provisional patent application Ser. No. 60/868,756, filed Dec. 6, 2006. The foregoing application is hereby incorporated by reference into the present application in its entirety.

FIELD OF THE INVENTION

The invention relates generally to the structure and use of radiofrequency electrosurgical apparatus for the treatment of tissue.

BACKGROUND

The delivery of radio frequency (RF) energy to target regions within solid tissue is known for a variety of purposes of particular interest to the present invention. In one particular application, RF energy may be delivered to diseased regions (e.g., tumors) for the purpose of ablating predictable volumes of tissue with minimal patient trauma.

RF ablation of tumors is currently performed using one of two core technologies. The first technology uses a single needle electrode, which when attached to a RF generator, emits RF energy from an exposed, uninsulated portion of the electrode. The second technology utilizes multiple needle electrodes, which have been designed for the treatment and necrosis of tumors in the liver and other solid tissues. U.S. Pat. No. 6,379,353 discloses such a probe, referred to as a LeVeen Needle Electrode™, which comprises a cannula and an electrode deployment member reciprocatably mounted within the delivery cannula to alternately deploy an electrode array from the cannula and retract the electrode array within the cannula. Using either of the two technologies, the energy that is conveyed from the electrode(s) translates into ion agitation, which is converted into heat and induces cellular death via coagulation necrosis. The ablation probes of both technologies are typically designed to be percutaneously introduced into a patient in order to ablate the target tissue.

In theory, RF ablation can be used to sculpt precisely the volume of necrosis to match the extent of the tumor. By varying the power output and the type of electrical waveform, it is possible to control the extent of heating, and thus, the resulting ablation. However, the size of tissue coagulation created from a single electrode, and to a lesser extent a multiple electrode array, has been limited by heat dispersion. Increasing generator output, however, has been generally unsuccessful for increasing lesion diameter, because an increased wattage is associated with a local increase of temperature to more than 100° C., which induces tissue vaporization and charring. This, then, decreases the moisture concentration of the tissue, and increases local tissue impedance, limiting RF deposition, and therefore heat diffusion and associated coagulation necrosis.

Currently, RF generators are designed to minimize the time required to create large ablation volumes, while avoiding tissue vaporization and charring.

These RF generators output and increase/decrease energy (i.e., power, current, voltage) in a consistent and steady manner. For example, as illustrated in FIG. 1, an energy output from an exemplary RF generator is maintained at a constant high level until a rise in tissue impedance or temperature indicating that an endpoint (i.e., largest volume of dessicated tissue with minimal to no charring) has been reached, after which the energy output steadily decreases. As another example, as illustrated in FIG. 2, an energy output from an exemplary RF generator steadily increases until a rise in tissue impedance or temperature indicated that an endpoint has been reached, after which the energy output steadily decreases.

While these RF generators efficiently provide large ablation volumes without tissue charring, it would be desirable to further decrease the ablation procedure time.

SUMMARY OF THE INVENTION

In accordance with a first aspect of the present inventions, a method of treating tissue (e.g., a tumor) within a patient is provided. The method comprises delivering ablation energy (e.g., radio frequency (RF) energy) to the tissue and sensing a physiological parameter (e.g., impedance and/or temperature) indicative of a change in moisture concentration of the tissue. The method further comprises alternately pulsing the ablation energy on and off to generate an energy pulse train. The ablation energy is pulsed on if the sensed physiological parameter crosses a threshold value indicative of an increase in the moisture concentration, and is pulsed off if the sensed physiological parameter crosses a threshold value indicative of a decrease in the moisture concentration. While the present inventions should not be so limited in their broadest aspects, the alternate pulsing of the ablation energy in accordance with increases and decreases in the moisture concentration of the tissue maximizes the amount of ablation energy that can be applied to the tissue after the tissue begins to lose moisture content.

An optional method further comprises amplitude modulating the ablation energy based on a width of a pulse within the energy pulse train; for example, by decreasing the amplitude of the ablation energy if the width of the pulse decreases below a threshold value. While the present inventions should not be so limited in their broadest aspects, decreasing the ablation energy ensures that the widths of pulses in the energy pulse train will be sufficient to deliver effective ablation energy to the tissue. In one method, the energy pulse train comprises pulses having a width equal to or greater than 1 second. In another method, the energy pulse train comprises pulses having differing widths that gradually decrease in amplitude. For example, the energy pulse train may comprise sets of pulses that gradually decrease in amplitude, with each pulse set including pulses having differing widths of the same amplitude.

In accordance with a second aspect of the present inventions, an ablation energy generator is provided. The ablation energy generator comprises an energy source (e.g., an RF energy source) for outputting ablation energy, and control circuitry for generating an energy pulse train in the same manner described above. In one embodiment, the control circuitry includes a controller configured for generating a trigger-on signal when the sensed physiological parameter crosses the threshold value indicative of an increase in the moisture concentration, and generating a trigger-off signal when the sensed physiological parameter crosses the threshold value indicative of a decrease in the moisture concentration. The control circuitry may further include a pulse modulator configured for pulsing the ablation energy on in response to the trigger-on signal, and pulsing the ablation energy off in response to the trigger-off signal.

In the case where amplitude modulation of the ablation energy is desired, the controller may further be configured for generating an amplitude reduction signal if a pulse within the energy pulse train is below a threshold value, in which case, the control circuitry may further comprise an amplitude modulator configured for decreasing the amplitude of the ablation energy in response to the amplitude reduction signal.

In accordance with a third aspect of the present inventions, a method of treating tissue (e.g., a tumor) within a patient is provided. The method comprises delivering ablation energy (e.g., radio frequency (RF) energy) to the tissue and sensing a physiological parameter (e.g., impedance and/or temperature). The method further comprises alternately pulsing the ablation energy on and off to generate an energy pulse train. The ablation energy is pulsed on when the sensed physiological parameter drops below a first one or more threshold values, and is pulsed off when the sensed physiological parameter rises above a second one or more threshold values.

While the present inventions should not be so limited in their broadest aspects, the alternate pulsing of the ablation energy in accordance with changes in a sensed physiological parameter maximizes the amount of ablation energy that can be applied to the tissue after the physiological parameter begins to rise. In some embodiments, the characteristics of the pulse train may be similar to the pulse train characteristics described. In other embodiment, the ablation energy may be amplitude modulated based on a width of a pulse within the energy pulse train with the accompanying advantages described above.

In accordance with a fourth aspect of the present inventions, an ablation energy generator is provided. The ablation energy generator comprises an energy source (e.g., an RF energy source) for outputting ablation energy, and control circuitry for generating an energy pulse train in the same manner described above. In one embodiment, the control circuitry includes a controller configured for generating a trigger-on signal when the sensed physiological parameter drops below the first threshold value, and for generating a trigger-off signal when the sensed physiological parameter rises above the second threshold value. The control circuitry may further include a pulse modulator configured for pulsing the ablation energy on in response to the trigger-on signal, and pulsing the ablation energy off in response to the trigger-off signal.

In the case where amplitude modulation of the ablation energy is desired, the controller may further be configured for generating an amplitude reduction signal if a pulse within the energy pulse train is below a threshold value, in which case, the control circuitry may further comprise an amplitude modulator configured for decreasing the amplitude of the ablation energy in response to the amplitude reduction signal.

Other and further aspects and features of the invention will be evident from reading the following detailed description of the preferred embodiments, which are intended to illustrate, not limit, the invention.

BRIEF DESCRIPTION OF DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIG. 3 is a perspective view of a tissue ablation system constructed in accordance with a preferred embodiment of the present invention;

FIG. 4 is a partially cutaway side view of an ablation probe used in the tissue ablation system of FIG. 3, wherein an array of electrode tines is particularly shown retracted;

FIG. 5 is a partially cutaway side view of an ablation probe used in the tissue ablation system of FIG. 3, wherein an array of electrode tines is particularly shown deployed;

DETAILED DESCRIPTION OF THE ILLUSTRATED EMBODIMENTS

Figure 1:
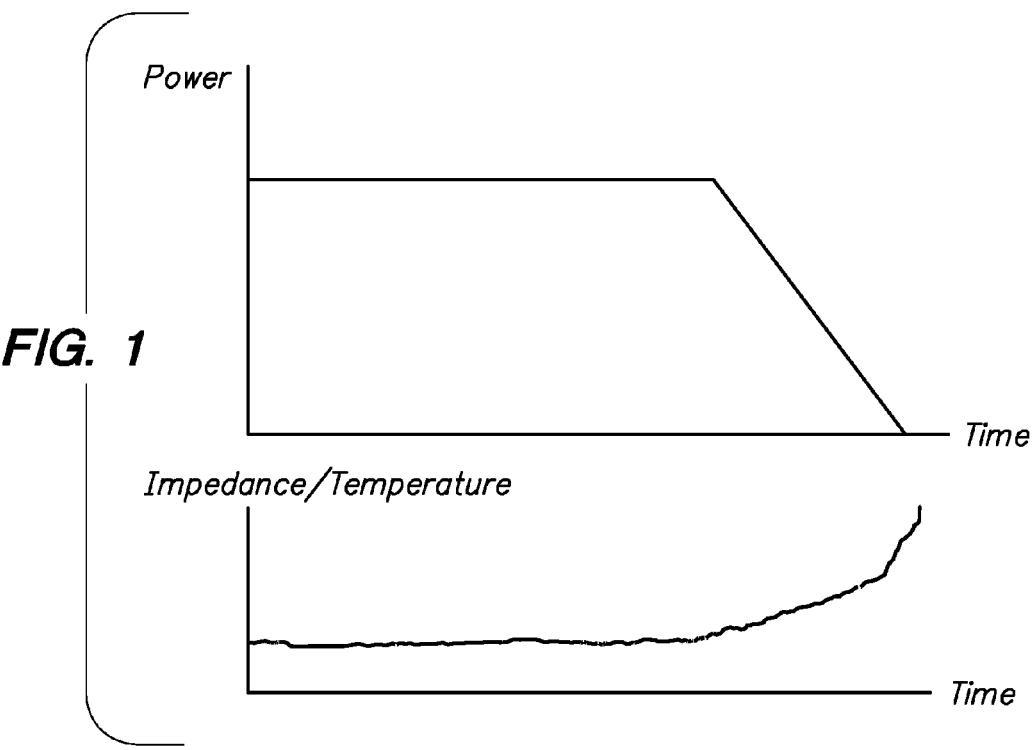
FIG. 1 is a plot of a prior art radio frequency (RF) ablation waveform.

Referring generally to FIG. 3, a tissue ablation system 10 constructed in accordance with one embodiment of the present inventions will be described. The tissue ablation system 10 generally includes an ablation probe 12 for introduction into the body of a patient for ablative treatment of target tissue, a radio frequency (RF) generator 14 configured for generating and providing RF power to the ablation probe 12 via a standard RF cable 16.

Referring specifically now to FIGS. 4 and 5, the probe 12 includes an elongate cannula 18 having a proximal end 20, a distal end 22, and a central lumen 24; a probe shaft 26 slidably disposed within the cannula lumen 24 and having a proximal end 28 and a distal end 30; and an array of electrode tines 32 carried by the distal end 28 of the probe shaft 26. The cannula 18 may be rigid, semi-rigid, or flexible depending upon the designed means for introducing the cannula 18 to the target tissue. The probe shaft 26 is composed of a suitably rigid material, such as plastic, metal or the like.

As best shown in FIG. 5, the probe 12 further comprises a physiological sensor 33 carried by the distal end 28 of the probe shaft 26. Thus, the physiological sensor 33 will be adjacent the tissue that is ablated by the electrode tines 32. The physiological sensor 33 may be any type of sensor that measures a physiological parameter indicative of the moisture concentration of the tissue to be ablated, but in the illustrated embodiment, it takes the form of an impedance sensor (which may be the electrodes themselves) and/or a temperature sensor. As will be described in further detail below, the RF generator 14 pulse modulates RF energy based on the physiological parameter(s) sensed by the physiological sensor 33 to provide for a more efficient tissue ablation process.

The probe 12 further includes a handle assembly 34, which includes a handle member 36 mounted to the proximal end 26 of the probe shaft 26, and a handle sleeve 38 mounted to the proximal end 20 of the cannula 18. The handle member 36 is slidably engaged with the handle sleeve 38 (and the cannula 18). The handle member 36 and handle sleeve 38 can be composed of any suitable rigid material, such as, e.g., metal, plastic, or the like. The handle assembly 34 also includes an electrical connector 40 mounted within the handle member 36. The electrical connector 40 is electrically coupled to the electrode array 32, e.g., via the probe shaft 26 (which will be electrically conductive) or separate wires (not shown). The electrical connector 40 is also electrically coupled to the physiological sensor 33 via wires (not shown). The electrical connector 40 is configured for mating with the proximal end of the RF cable 16 (shown in FIG. 3). Alternatively, the RF cable 16 may be hardwired within the handle member 36.

It can be appreciated that longitudinal translation of the probe shaft 26 relative to the cannula 18 in a distal direction 42, by holding the handle sleeve 38 and displacing the handle member 36 in the distal direction 42, deploys the electrode array 32 from the distal end 22 of the cannula 18 (FIG. 5), and longitudinal translation of the probe shaft 26 relative to the cannula 18 in a proximal direction 44, by holding the handle sleeve 38 and displacing the handle member 36 in the proximal direction 44, retracts the probe shaft 26 and the electrode array 32 into the distal end 22 of the cannula 18 (FIG. 4).

In the illustrated embodiment, the RF current is delivered to the electrode array 32 in a monopolar fashion, which means that current will pass from the electrode array 32, which is configured to concentrate the energy flux in order to have an injurious effect on the surrounding tissue, and a dispersive electrode (not shown), which is located remotely from the electrode array 32 and has a sufficiently large area (typically 130 cm$^2$ for an adult), so that the current density is low and non-injurious to surrounding tissue. In the illustrated embodiment, the dispersive electrode may be attached externally to the patient, e.g., using a contact pad placed on the patient's flank. Alternatively, the RF current is delivered to the electrode array 32 in a multipolar (e.g., bipolar) fashion, which means that current will pass between positive ones of the electrodes 32 and negative ones of the electrodes 32, thereby concentrating the energy flux in order to have an injurious effect on the tissue between the electrodes of the array 32. In this case, the positive electrodes will be electrically insulated from the negative electrodes.

Further details regarding electrode array-type probe arrangements are disclosed in U.S. Pat. No. 6,379,353, which is hereby expressly incorporated by reference. It should be noted that the tissue ablation probe 12 illustrated in FIGS. 4 and 5 is only one type of ablation probe that can be used with the tissue treatment system 10. For example, a single needle electrode probe may be used as well.

The RF generator 14 may be general purpose electrosurgical power supply operating at a frequency in the range from 300 kHz to 9.5 MHz, with a conventional sinusoidal or non-sinusoidal wave form, although other wave forms would also be acceptable. The output will usually be from 2 W to 300 W. Significantly, the RF generator 14 differs from conventional RF generators in that it maintains the maximum level of the delivered ablation energy during a longer time period after the moisture concentration of the tissue begins to decrease by pulse-modulating and amplitude-modulating the outputted RF ablation energy based on the physiological tissue parameters sensed by the ablation probe 12.

Figure 6:
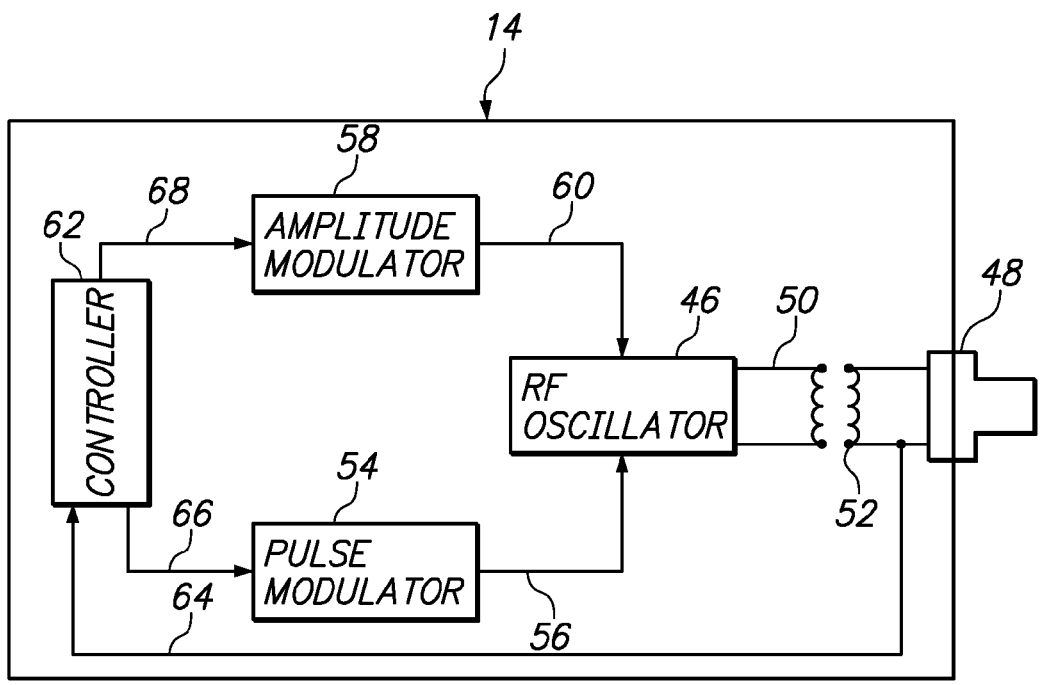
FIG. 6 is a block diagram of the control circuitry of an RF generator used in the tissue ablation system of FIG. 3.

Referring to FIG. 6, the RF generator 14 comprises an RF energy source, and in particular, an RF oscillator 46 coupled to an RF connector 48 via output lines 50 and a transformer 52. The RF generator 14 further comprises a pulse modulator 54 that conveys a pulse modulating signal to the RF oscillator 46 via line 56. In response, the RF oscillator 46 outputs a pulsed RF energy wave; i.e., an RF energy wave that is alternately pulsed on and off to produce an RF energy pulse train. The RF energy is considered to be pulsed on if has a magnitude that effects tissue ablation and is considered to be pulsed off if has a magnitude (which may include zero) that does not effect tissue ablation. In the illustrated embodiment, the magnitude of the RF energy is zero when pulsed off, although the magnitude of the RF energy can be a value other than zero (e.g., 1-5% of maximum) and still be considered to be pulsed off if it not at a level sufficient to ablate tissue. The RF generator 14 also comprises an amplitude modulator 58 that conveys a drive signal to the RF oscillator 46 via line 60. In response, the pulsed RF energy wave output by the RF oscillator 46 has an amplitude that can be varied.

The RF generator 14 further comprises a controller 62 that controls the output of the RF oscillator 46 by receiving over line 64 via the connector 48 physiological parameters sensed by the physiological sensor 33 located on the ablation probe 12 (shown in FIG. 5), and conveying trigger signals to the pulse modulator 54 and the amplitude modulator 58 via respective lines 66, 68 in response to the sensed physiological parameters. In particular, the controller 62 conveys a pulse-on trigger signal to the pulse modulator 54 in order to pulse the ablation energy output by the RF oscillator 46 on, and conveys a pulse-off trigger signal to the pulse modulator 54 in order to pulse the ablation energy output by the RF oscillator 46 off. The controller 62 conveys an amplitude decrease trigger signal to the amplitude modulator 58 to decrease the level of the ablation energy output by the RF oscillator 46, and conveys an amplitude increase trigger signal to the amplitude modulator 58 to increase the level of the ablation energy output by the RF oscillator 46. In the case where the sensed physiological parameter is tissue impedance, the controller 62 may include voltage or current sensing circuitry (not shown) for sensing the voltage or current at the tissue and calculating tissue impedance based on this voltage or current measurement.

Figure 7:
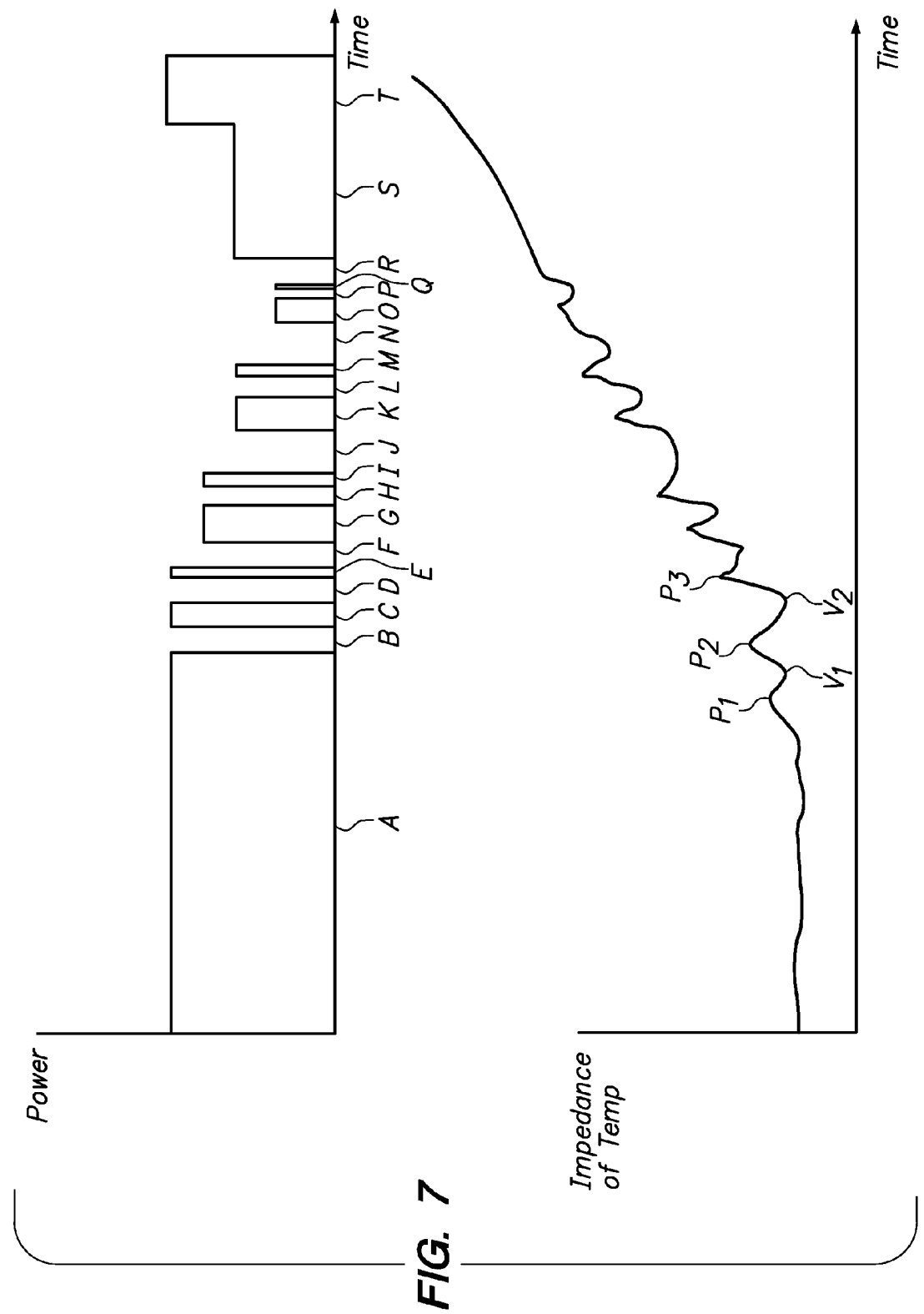
FIG. 7 is a plot of an RF ablation waveform output by the RF generator of FIG. 6.

The operation of the RF generator 14 in pulse-modulating and amplitude-modulating the ablation energy delivered to the tissue will now be described with reference to an ablation energy waveform illustrated in FIG. 7.

Figure 2:
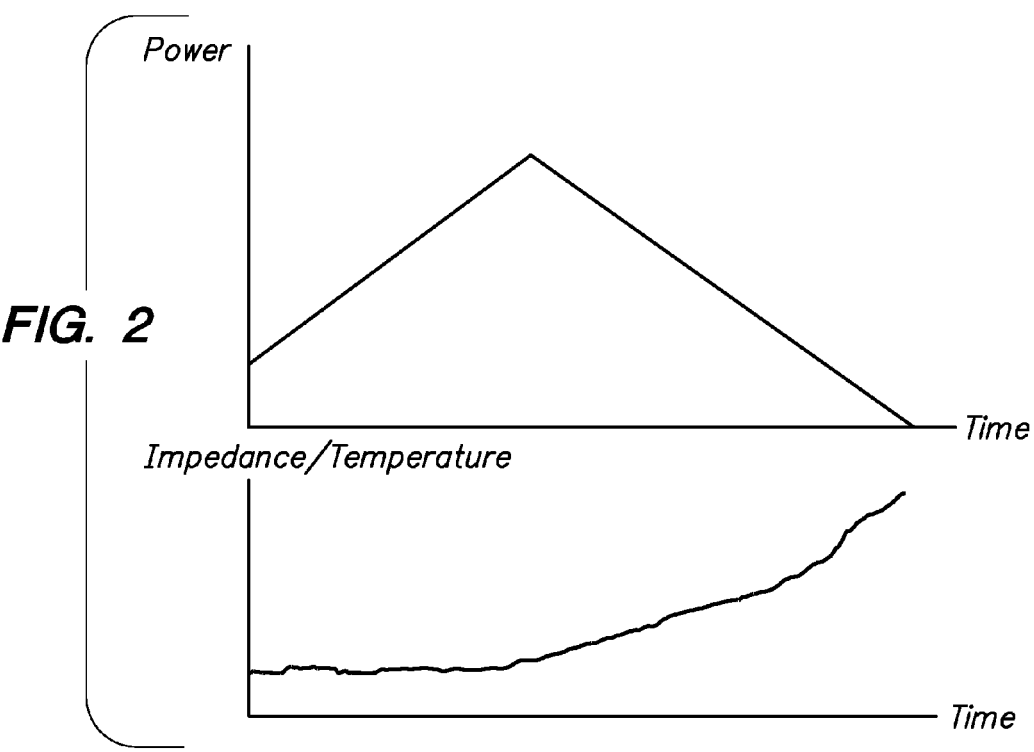
FIG. 2 is a plot of another prior art RF ablation waveform.

At the beginning of the tissue ablation process, the level of the ablation energy output by the RF generator 14 is maintained at a constant level during time period A. The level at which the ablation energy is maintained may be dictated by the user or the RF generator 14, itself. In one embodiment, the amplitude of the initial ablation current is 3 amps. Alternatively, the level of the ablation energy output by the RF generator 14 is steadily increased in a manner illustrated in FIG. 2. In any event, the controller 62 conveys a signal to the amplitude modulator 58, which drives the RF oscillator 46 in accordance with the desired initial ablation energy level.

Next, the ablation energy delivered to the tissue is alternately pulsed on and off to generate an energy pulse train based on the moisture concentration of the tissue. In particular, when the physiological parameter, and in particular, the impedance/temperature level sensed by the ablation probe 12 rises above a first threshold value (as shown by the peak p1 in the impedance/temperature curve of FIG. 7), indicating a substantial increase in vapor within the tissue, and therefore a substantial decrease in the moisture concentration of the tissue relative to the base-line moisture concentration of the tissue at the beginning of time period A, the ablation energy is pulsed off. That is, the controller 62 conveys a pulse-off trigger signal to the pulse modulator 54, which in turn, pulses off the RF oscillator 46, so that no ablation energy, or at least no effective ablation energy, is delivered to the tissue.

During the time period that the ablation energy is pulsed off, as indicated by time period B, the vapor previously built up during time period A condenses, thereby resulting in an increase in the moisture concentration of the tissue relative to the moisture concentration of the tissue at the beginning of time period B. When the impedance/temperature level sensed by the ablation probe 12 drops below a second threshold value (as shown by the valley v1 in the impedance/temperature curve of FIG. 7), indicating a substantial decrease in vapor within the tissue, and therefore a substantial increase in the moisture concentration of the tissue relative to the moisture concentration of the tissue at the beginning of time period B, the ablation energy is pulsed on. That is, the controller 62 conveys a pulse-on trigger signal to the pulse modulator 54, which in turn, pulses on the RF oscillator 46, so that an effective amount of ablation energy is delivered to the tissue.

During the time period that the ablation energy is pulsed on, as indicated by time period C, the vapor previously condensed during time period B builds back up, thereby resulting in a decrease in the moisture concentration of the tissue relative to the moisture concentration of the tissue at the beginning of time period C. When the impedance/temperature level sensed by the ablation probe 12 rises above a third threshold value (as shown by the peak p2 in the impedance/temperature curve of FIG. 7), indicating a substantial increase in vapor within the tissue, and therefore a substantial decrease in the moisture concentration of the tissue relative to the moisture concentration of the tissue at the beginning of time period C, the ablation energy is pulsed off. That is, the controller 62 conveys a pulse-off trigger signal to the pulse modulator 54, which in turn, pulses off the RF oscillator 46, so that no ablation energy, or at least no effective ablation energy, is delivered to the tissue.

During the time period that the ablation energy is pulsed off, as indicated by time period D, the vapor previously built up during time period C condenses, thereby resulting in an increase in the moisture concentration of the tissue relative to the moisture concentration of the tissue at the beginning of time period D. When the impedance/temperature level sensed by the ablation probe 12 drops below a fourth threshold value (as shown by the valley v2 in the impedance/temperature curve of FIG. 7), indicating a substantial decrease in vapor within the tissue, and therefore a substantial increase in the moisture concentration of the tissue relative to the moisture concentration of the tissue at the beginning of time period D, the ablation energy is pulsed on. That is, the controller 62 conveys a pulse-on trigger signal to the pulse modulator 54, which in turn, pulses on the RF oscillator 46, so that an effective amount of ablation energy is delivered to the tissue.

During the time period that the ablation energy is pulsed on, as indicated by time period E, the vapor previously condensed during time period D builds back up, thereby resulting in a decrease in the moisture concentration of the tissue relative to the moisture concentration of the tissue at the beginning of time period E. When the impedance/temperature level sensed by the ablation probe 12 rises above a fifth threshold value (as shown by the peak p3 in the impedance/temperature curve of FIG. 7), indicating a substantial increase in vapor within the tissue, and therefore a substantial decrease in the moisture concentration of the tissue relative to the moisture concentration of the tissue at the beginning of time period E, the ablation energy is pulsed off. That is, the controller 62 conveys a pulse-off trigger signal to the pulse modulator 54, which in turn, pulses off the RF oscillator 46, so that no ablation energy, or at least no effective ablation energy, is delivered to the tissue.

Each of the threshold values may be selected to be any suitable value. In the illustrated embodiment, the threshold values are determined relative to each other. That is, the first threshold value used to determine when to pulse the ablation energy off at the end of time period A is a value equal to a certain percentage or predetermined offset above the baseline value of the impedance/temperature at the beginning of time period A; the third threshold value used to determine when to pulse the ablation energy off at the end of time period C is a value equal to a percentage or predetermined offset above the first threshold value; and the fifth threshold value used to determine when to pulse the ablation energy off at the end of time period E is a value equal to a percentage or predetermined offset above the third threshold value. The second threshold value used to determine when to pulse the ablation energy on at the end of time period B is a value equal to a percentage or predetermined offset below the first threshold value (but above the baseline value of the impedance/temperature at the beginning of time period A); and the fourth threshold value used to determine when to pulse the ablation energy on at the end of time period D is a value equal to a percentage or predetermined offset below the third threshold value (but above the second threshold value). In alternative embodiments, the threshold values are set at predetermined absolute values. While, in the illustrated embodiment, all of the threshold values differ from each other, in alternative embodiments, at least some of the threshold values may be the same.

The process performed with respect to the portion of the energy pulse train in time periods B-E are repeated for respective portions of the energy pulse trains in time periods F-I, time periods J-M, and time periods N-Q, with the exception that the amplitudes of the pulses in the pulse trains gradually decrease in amplitude, so as to further maximize the delivery of ablation energy when the widths of the pulses become too small (e.g., 1 second) to provide effective delivery of ablation energy. In particular, because the vapor concentration of the tissue tends to more steeply rise with each pulse in a pulse train, the widths of the pulses will decrease over time unless the amplitude of the energy is decreased. Thus, as can be seen in FIG. 7, the energy pulse train comprises pulse sets that gradually decrease in amplitude, with each pulse set having pulses of differing widths of the same amplitude.

Thus, in the illustrated embodiment, the controller 62 conveys an amplitude decrease trigger signal to the amplitude modulator 58, which in turn, decreases the amplitude of the drive signal to the RF oscillator 46, so that the amplitude of the ablation energy delivered to the tissue is decreased. In the illustrated embodiment, the level to which the ablation energy is decreased is based on a percentage or offset of the immediately previous level of the ablation energy (e.g., 20% or 0.5 amp drop in magnitude)—although in alternative embodiments, the ablation energy may be gradually decreased to predetermined absolute levels.

In an optional embodiment, after the amplitude level and width of a pulse has been reduced below a certain threshold, indicating that the tissue ablation process is completed or near completion, the ablation energy is pulsed off for the time period R, and then the amplitude of the ablation energy is increased to a predetermined level and left there for a predetermined period of time S to ensure that the tissue has been completely ablated. In this case, the controller 62 conveys an amplitude increase trigger signal to the amplitude modulator 58, which in turn, increases the amplitude of the drive signal to the RF oscillator 46, so that the amplitude of the ablation energy delivered to the tissue is increased.

The ablation energy may then be further increased during time period T to a level equal to the initial level, during which time the vapor builds back up in the tissue, thereby resulting in a decrease in the moisture concentration of the tissue relative to the moisture concentration of the tissue at the beginning of time period T. In the illustrated embodiment, the controller 62 conveys an amplitude increase trigger signal to the amplitude modulator 58, which in turn, increases the amplitude of the drive signal to the RF oscillator 46, so that the amplitude of the ablation energy delivered to the tissue is increased.

When the impedance/temperature level sensed by the ablation probe 12 rises above a sixth threshold value, indicating a substantial increase in vapor within the tissue, and therefore a substantial decrease in the moisture concentration of the tissue relative to the moisture concentration of the tissue at the beginning of time period T, the ablation energy is turned off, thereby indicating to the user that the ablation process is completed.

While the pulsing of the ablation energy has been described as being based on a change in moisture concentration of the tissue, pulsing of the ablation energy can be based solely on a change in a physiological parameter not correlated to moisture concentration in tissue. For example, at lower temperature levels where vaporization does not occur, but tissue ablation does (e.g., above 50-60° C.), the pulsing of the ablation energy may be based on measured temperature at this range. For example, the ablation energy may be pulsed off when the temperature rises above 70° C. and pulsed on when the temperature drops below 50° C.

Figure 8A:
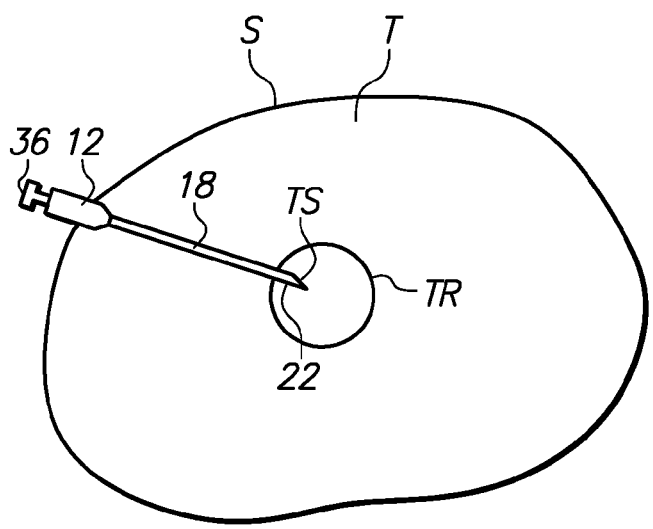
FIGS. 8A-8C are side views illustrating a method of ablating tissue using the tissue ablation system of FIG. 1.
Figure 8B:
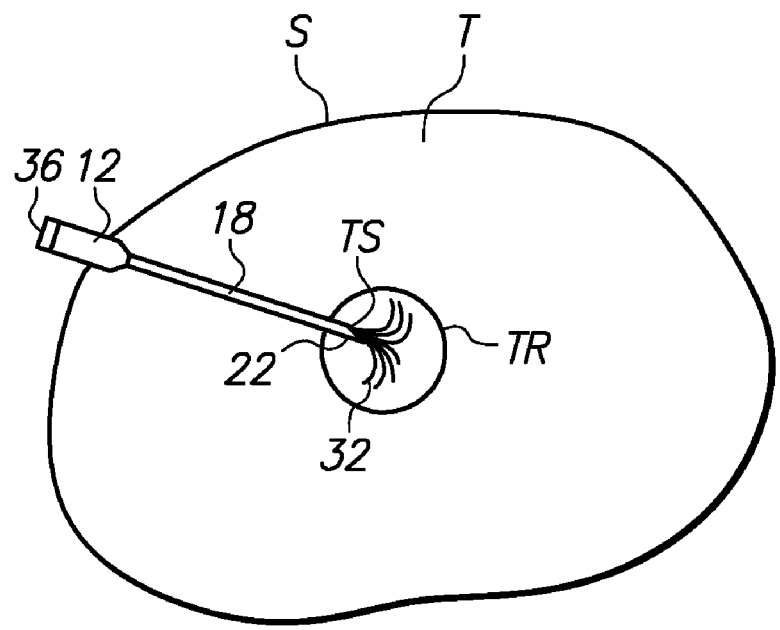

Referring now to FIGS. 8A and 8B, the operation of the tissue ablation system 10 is described in treating a treatment region TR within tissue T located beneath the skin or an organ surface S of a patient. Although a single treatment region TR is illustrated for purposes of brevity, the tissue ablation system 10 may alternatively be used to treat multiple treatment regions TR. The ablation probe 12 is first introduced through the tissue T, so that the distal end 22 of the cannula 18 is located at the target site TS within the treatment region TR (FIG. 8A).

This can be accomplished using any one of a variety of techniques. In the preferred method, the ablation probe 12 is percutaneously introduced to the treatment region TR directly through the patient's skin or through an open surgical incision. In this case, the distal end of the cannula 18 may be sharpened to facilitates introduction of the ablation probe 12 to the treatment region TR. In such cases, it is desirable that the cannula 18 be sufficiently rigid, i.e., have a sufficient column strength, so that it can be accurately advanced through tissue T. In other cases, the cannula 18 may be introduced using an internal stylet that is subsequently exchanged for the probe shaft 26. In this latter case, the probe shaft 26 can be relatively flexible, since the initial column strength will be provided by the stylet. More alternatively, a component or element may be provided for introducing each cannula 18 to the respective target ablation site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 18 can then be introduced through the sheath lumen, so that the distal end 22 of the cannula 18 advances from the sheath into the target ablation site TS.

Figure 8C:
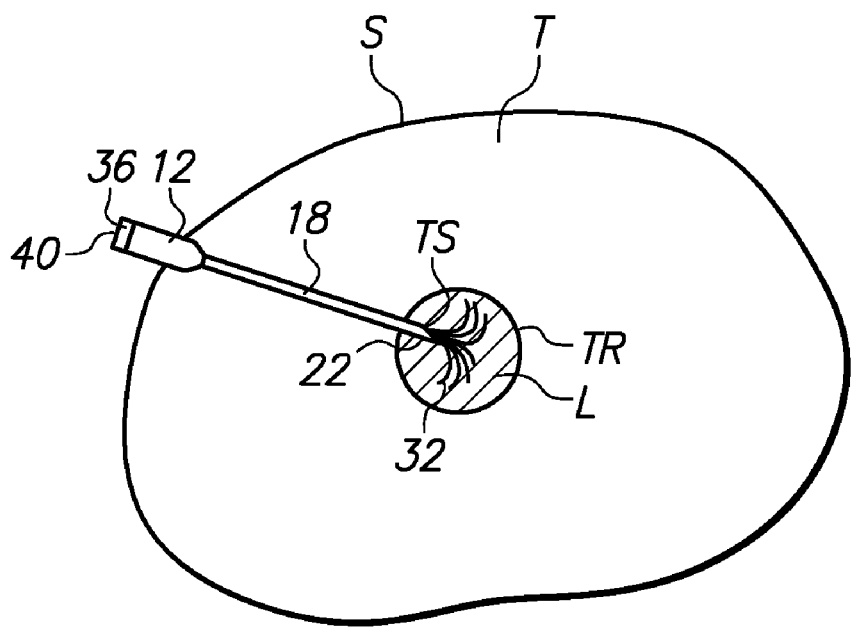

Once the ablation probe 12 is properly positioned, the handle member 36 of the ablation probe 12 is distally advanced to deploy the electrode array 32 radially outward from the distal end 22 of the respective cannula 18 until the electrode array 32 fully everts within the respective target tissue site TS (FIG. 8B). Once the electrode array 32 is fully deployed into the target ablation site TS, the cable 16 of the RF generator 14 (shown in FIG. 3) is then connected to the electrical connector 40 of the ablation probe 12, and then operated to transmit RF energy to the electrode array 32 in accordance with the waveform illustrated in FIG. 7, thereby ablating the treatment region TR (FIG. 8C). As a result, a lesion L will be created, which will eventually expand to include the entire treatment region TR.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed:

1. A method of treating tissue within a patient, comprising:
delivering ablation energy to the tissue;
sensing a physiological parameter indicative of change in moisture concentration of the tissue;
alternately pulsing the ablation energy on and off to generate an energy pulse train, wherein the ablation energy is pulsed on if the sensed physiological parameter crosses a threshold value indicative of an increase in the moisture concentration, and is pulsed off if the sensed physiological parameter crosses a threshold value indicative of a decrease in the moisture concentration; and
amplitude modulating the ablation energy based on a width of a pulse within the energy pulse train.

2. The method of claim 1, wherein the physiological parameter is one or more of a temperature and an impedance.

3. The method of claim 1, wherein the amplitude modulation of the ablation energy comprises decreasing the amplitude of the ablation energy if the width of the pulse decreases below a threshold value.

4. The method of claim 1, wherein the energy pulse train comprises pulses having a width equal to or greater than 1 second.

5. The method of claim 1, wherein the energy pulse train comprises pulses having differing widths.

6. The method of claim 1, wherein the energy pulse train comprises pulses that gradually decrease in amplitude.

7. The method of claim 1, wherein the energy pulse train comprises sets of pulses, each pulse set including pulses having differing widths of the same amplitude, the pulse sets gradually decreasing in amplitude.

8. The method of claim 1, wherein the ablation energy comprises radio frequency (RF) ablation energy.

9. A method of treating tissue within a patient, comprising:
delivering ablation energy to the tissue;
sensing a change in a physiological parameter of the tissue;
alternately pulsing the ablation energy on and off to generate an energy pulse train, wherein the ablation energy is pulsed on when the sensed physiological parameter drops below a first one or more threshold values, and is pulsed off when the sensed physiological parameter rises above a second one or more threshold values; and
amplitude modulating the ablation energy based on a width of a pulse within the energy pulse train.

10. The method of claim 9, wherein the physiological parameter is one or more of a temperature and an impedance.

11. The method of claim 9, wherein the amplitude modulation of the ablation energy comprises decreasing the amplitude of the ablation energy if the width of the pulse decreases below a threshold value.

12. The method of claim 9, wherein the energy pulse train comprises pulses having a width equal to or greater than 1 second.

13. The method of claim 9, wherein the energy pulse train comprises pulses having differing widths.

14. The method of claim 9, wherein the energy pulse train comprises pulses that gradually decrease in amplitude.

15. The method of claim 9, wherein the energy pulse train comprises sets of pulses, each pulse set including pulses having differing widths of the same amplitude, the pulse sets gradually decreasing in amplitude.

16. The method of claim 9, wherein the first one or more threshold values comprises a first plurality of threshold values that differ from each other, and the second one or more threshold values comprises a second plurality of threshold values that differ from each other.

17. The method of claim 16, wherein the first plurality of threshold values gradually increase, and the second plurality of threshold values gradually increase.

18. The method of claim 9, wherein the ablation energy comprises radio frequency (RF) ablation energy.

19. An ablation energy generator, comprising:
an energy source for outputting ablation energy; and
control circuitry configured for receiving a sensed physiological parameter indicative of change in moisture concentration of the tissue, and for alternately pulsing the ablation energy on and off to generate an energy pulse train, wherein the ablation energy is pulsed on if the sensed physiological parameter crosses a threshold value indicative of an increase in the moisture concentration, and is pulsed off if the sensed physiological parameter crosses a threshold value indicative of a decrease in the moisture concentration, and wherein the control circuitry is further configured for amplitude modulating the ablation energy based on a width of a pulse within the energy pulse train.

20. The ablation energy generator of claim 19, wherein the physiological parameter is one or more of a temperature and an impedance.

21. The ablation energy generator of claim 19, wherein the control circuitry is configured for amplitude modulating the ablation energy by decreasing the amplitude of the ablation energy if the width of the pulse decreases below a threshold value.

22. The ablation energy generator of claim 19, wherein the control circuitry includes a controller configured for generating a trigger-on signal when the sensed physiological parameter crosses the threshold value indicative of an increase in the moisture concentration, and generating a trigger-off signal when the sensed physiological parameter crosses the threshold value indicative of a decrease in the moisture concentration, and a pulse modulator configured for pulsing the ablation energy on in response to the trigger-on signal, and pulsing the ablation energy off in response to the trigger-off signal.

23. The ablation energy generator of claim 19, wherein the controller is configured for generating an amplitude reduction signal if a pulse within the energy pulse train is below a threshold value, and wherein the control circuitry further comprises an amplitude modulator configured for decreasing the amplitude of the ablation energy in response to the amplitude reduction signal.

24. The ablation energy generator of claim 19, wherein the energy pulse train comprises pulses having a width equal to or greater than 1 second.

25. The ablation energy generator of claim 19, wherein the energy pulse train comprises pulses having differing widths.

26. The ablation energy generator of claim 19, wherein the energy pulse train comprises pulses that gradually decreases in amplitude.

27. The ablation energy generator of claim 19, wherein the energy pulse train comprises sets of pulses, each pulse set including pulses having differing widths of the same amplitude, the pulse sets gradually decreasing in amplitude.

28. The ablation energy generator of claim 19, wherein the energy source is a radio frequency (RF) energy source.

29. An ablation energy generator, comprising:
an energy source for outputting ablation energy; and
control circuitry configured for receiving a sensed physiological parameter, and for alternately pulsing the ablation energy on and off to generate an energy pulse train, wherein the ablation energy is pulsed on when the sensed physiological parameter drops below a first one or more threshold values, and is pulsed off when the sensed physiological parameter rises above a second one or more threshold values, and wherein the controller is configured for generating an amplitude reduction signal if a pulse within the energy pulse train is below a pulse width threshold value, and wherein the control circuitry further comprises an amplitude modulator configured for decreasing the amplitude of the ablation energy in response to the amplitude reduction signal.

30. The ablation energy generator of claim 29, wherein the physiological parameter is one or more of a temperature and an impedance.

31. The ablation energy generator of claim 29, wherein the control circuitry includes a controller configured for generating a trigger-on signal when the sensed physiological parameter drops below the first one or more threshold values, and for generating a trigger-off signal when the sensed physiological parameter rises above the second one or more threshold values, and a pulse modulator configured for pulsing the ablation energy on in response to the trigger-on signal, and pulsing the ablation energy off in response to the trigger-off signal.

32. The ablation energy generator of claim 29, wherein the energy pulse train comprises pulses having a width equal to or greater than 1 second.

33. The ablation energy generator of claim 29, wherein the energy pulse train comprises pulses having differing widths.

34. The ablation energy generator of claim 29, wherein the energy pulse train comprises pulses that gradually decreases in amplitude.

35. The ablation energy generator of claim 29, wherein the energy pulse train comprises sets of pulses, each pulse set including pulses having differing widths of the same amplitude, the pulse sets gradually decreasing in amplitude.

36. The ablation energy generator of claim 29, wherein the first one or more threshold values comprises a first plurality of threshold values that differ from each other, and the second one or more threshold values comprises a second plurality of threshold values that differ from each other.

37. The ablation energy generator of claim 36, wherein the first plurality of threshold values gradually increase, and the second plurality of threshold values gradually increase.

38. The ablation energy generator of claim 29, wherein the energy source is a radio frequency (RF) energy source.

39. An ablation energy generator, comprising:
an energy source for outputting ablation energy; and
control circuitry configured for receiving a sensed physiological parameter, and for alternately pulsing the ablation energy on and off to generate an energy pulse train, wherein the ablation energy is pulsed on when the sensed physiological parameter drops below a first one or more threshold values, and is pulsed off when the sensed physiological parameter rises above a second one or more threshold values, and wherein the first one or more threshold values comprises a first plurality of threshold values that differ from each other, and the second one or more threshold values comprises a second plurality of threshold values that differ from each other.

40. An ablation energy generator, comprising:

an energy source for outputting ablation energy; and control circuitry configured for receiving a sensed physiological parameter, and for alternately pulsing the ablation energy on and off to generate an energy pulse train, wherein the ablation energy is pulsed on when the sensed physiological parameter drops below a first one or more threshold values, and is pulsed off when the sensed physiological parameter rises above a second one or more threshold values, and wherein the first plurality of threshold values gradually increase, and the second plurality of threshold values gradually increase.

* * * * *